United States Patent [19]

Hellstrom et al.

[11] Patent Number: 5,134,075
[45] Date of Patent: Jul. 28, 1992

[54] MONOCLONAL ANTIBODY TO NOVEL ANTIGEN ASSOCIATED WITH HUMAN TUMORS

[75] Inventors: Karl E. Hellstrom; Ingegerd Hellstrom, both of Seattle; Hans Marquardt, Mercer Island; Yoshitaka Yoneyama, Bellevue, all of Wash.

[73] Assignee: Oncogen Limited Partnership, Seattle, Wash.

[21] Appl. No.: 312,640

[22] Filed: Feb. 17, 1989

[51] Int. Cl.$^5$ .................. C12N 5/00; C07K 15/28
[52] U.S. Cl. .................. 530/387.3; 435/70.21; 435/172.2; 530/387.9; 530/828; 530/388.85; 530/388.15; 530/391.3
[58] Field of Search .................. 530/387, 828; 435/172.2, 240.26, 240.27, 972, 70.21

[56] References Cited

U.S. PATENT DOCUMENTS

| | | |
|---|---|---|
| 4,474,893 | 10/1984 | Reading. |
| 4,507,391 | 3/1985 | Pukel et al.. |
| 4,579,827 | 4/1986 | Sukamoto et al. .................. 436/536 |
| 4,612,282 | 9/1986 | Schlom et al.. |
| 4,708,930 | 11/1987 | Kortright et al.. |
| 4,713,351 | 12/1987 | Knauf. |
| 4,737,579 | 4/1988 | Hellstrom et al.. |
| 4,753,894 | 6/1988 | Frankel et al. .................. 436/548 |

FOREIGN PATENT DOCUMENTS

| | | |
|---|---|---|
| 323802 | 7/1989 | European Pat. Off.. |
| 338846 | 10/1989 | European Pat. Off.. |
| A2186885 | 8/1987 | United Kingdom. |

OTHER PUBLICATIONS

Dippold et al., "Cell Surface Antigens of Human Malignant Melonoma:Definition Six Antigenic Systems with Mouse Monoclonal Antibodies", Proc. Natl. Acad. Sci. USA, 77(10) pp. 6114–6118 Oct. 1980.
Gerlach et al., Abstract #120979, Biol. Abstr 84(12) Dec. 15, 1987.
Sikora, "Human Monoclonal Antibodies", British Medical Bulletin, vol. 40 (3) pp. 209–212, 1984.
Hellstrom et al., "Monoclonal Mouse Antibodies Raised Against Human Lung Carcinoma" Cancer Research 46 pp. 3917–3923, Aug. 1986.
Papsidero, "Recent Progress in the Immunological Monitoring of Carcinomas Using Monoclonal Antibodies", Sem. Surg. Oncol., 1(4):171–81 (1985).
Schlom et al., "Potential Clinical Utility of Monoclonal Antibodies in the Management of Human Carcinomas", Important Adv. Oncol. 170–92 (1985).
Allum et al., "Monoclonal Antibodies in the Diagnosis and Treatment of Malignant Conditions" Surg. Ann 18:41–64 (1986).
Houghton, "Monoclonal Antibodies: Potential Applications to the Treatment of Cancer", Semin. Oncol. 13(2):165–79 (1986).
Fink et al., "Monoclonal Antibodies and Diagnostic Reagents for the Identification and Characterization of Human Tumor Antigens", Prog. Clin. Pathol., 9:121–33 (1984).
Johnston, "Applications of Monoclonal Antibodies in Clinical Cytology as Exemplified by Studies with Monoclonal Antibody B72.3", Acta. Cytol. 1(5):537–56 (1987).
Young et al., "Production of Monoclonal Antibodies Specific for Two Distinct Steric Portions of the Glycolipid Ganglio-N-triosylceramide (aslio GM2), J. Exp. Med. 150:1008–19 (1979).
Kniep et al., "Ganliotriaosylceramide (Asialo GM2), a Glycosphingolipid Marker for Cell Lines Derived From Patients with Hodgkins Disease", J. Immunol. 131(3):1591–94 (1983).
Rosen et al., "Analysis of Human Small Cell Lung Cancer Differentiation Antigens Using a Panel of Rat Monoclonal Antibodies", Cancer Res., 44:2052–61 (1984).
Varki et al., "Antigens Associated with a Human Lung Adenocarcinoma Defined by Monoclonal Antibodies" Cancer Res. 44:681–87 (1984).
Hellstrom et al., "Antitumor Effects of L6, an IgG2a Antibody that reacts with Most Human Carcinomas" Proc. Natl. Acad. Sci USA 83:7059–63 (1986).
Kohler and Milstein, "Continuous Cultures of Fused Cells Secreting Antibody of Predefined Specificity" Nature, 256:495 (1975).
Brown et al., "Structural Characterization of Human Melanoma-Associated Antigen p97 with Monolonal Antibodies" J. Immunol. 127(2):539–46 (1981).
Brown et al., "Protein Antigens of Normal and Malignant Human Cells Identified by Immunoprecipitation with Monoclonal Antibodies", J. Biolog. Chem., 255:4980–83 (1980).

(List continued on next page.)

Primary Examiner—Esther L. Kepplinger
Assistant Examiner—Carol E. Bidwell
Attorney, Agent, or Firm—SaraLynn Mandel

[57] ABSTRACT

The present invention is concerned with a novel monoclonal antibody which binds strongly to a protein antigen associated with human tumors, including carcinomas of the colon, breast, ovary and lung, as well as melanomas and sarcomas. The antibody binds to normal human cells to a much lesser degree than to tumor cells. The antibody finds use both in diagnostic methods such as the detection of malignant cells associated with tumors and in therapeutic methods for treatment of humans with tumors. Also disclosed is a novel 100,000 dalton glycoprotein antigen found on the cell surface of human tumor cells. The amino terminal amino acid sequence of this antigen is:

```
1           5              10
W—Y—T—V—N—S—A—Y—G—D—T—I—I—I—
         15           20          25
         —P—X—R—L—D—V—P—Q—N—L—M—F
``` in which X represents an unidentified amino acid.

21 Claims, No Drawings

OTHER PUBLICATIONS

Yeh et al., "Cell Surface Antigens of Human Melanoma Identified by Monoclonal Antibody" *Proc. Natl. Acad. Sci. USA* 76(6):2927-31 (1979).

Yeh et al., "A Cell-Surface Antigen Which is Present in the Ganglioside Fraction and Shared by Human Melanomas", *Int. J. Cancer* 29:269-75 (1982).

Zola, In Monoclonal Hybridoma Antibodies: Techniques and Applications, Hurrell (Ed.) pp. 51-52 (CRC Press 1982).

Shawler, "Human Immune Response to Multiple Injections of Murine Monoclonal IgG3" *J. Immunol.* 135:1530-35 (1985).

Oi et al., "Chimeric Antibodies", *Biotechnologies* 4(3):214-221 (1986).

Borrabaeck et al., "Human Monoclonal Antibodies Produced by Primary in vitro Immunization of Peripheral Blood Lymphocytes", *Proc. Natl. Acad. Sci USA* 85:3995-99 (1988).

Hellstrom et al., "Covalently Modified Antigens and Antibodies in Antibodies in Diagnosis and Therapy" Quash/Rodwell (Eds.), pp. 24-28 (Marcel Dekker, Inc.) (1989).

Bagshawe, "Tumour Markers-Where do we go from here?" *Br. J. Cancer* 48:167-75 (1983).

Rousseaux et al., in *Methods Enzymol*, 121:663-69, Academic Press, (1986).

Thammana et al., "Immunoglobulin Heavy Chain Class Switch from IgM to IgG in Ahybridoma" *Eur. J. Immunol.* 13:614 (1983).

Spira et al., "The Identification of Monoclonal Class Switch Variants by Sib Selection and an ELISA Assay" *J. Immunol. Meth.* 74:307-15 (1984).

Neuberger et al., "Recombinant Antibodies Possessing Novel Effector Functions" *Nature*, 312:604-08 (1984).

Nepom et al., "Anti-Idiotypic Antibodies and the Induction of Specific Tumor Immunity" *Cancer and Metastasis Reviews* 6:487-501 (1987).

Lee et al., "Monoclonal Antiidiotypic Antibodies Related to a Murine Oncofetal Bladder Tumor Antigen Induce Specific Cell-Modulated Tumor Immunity", *Proc. Acad. Sci (USA)* 82:6286-90 (1985).

Hakamori, "Tumor-Associated Carbohydrate Antigens", *Rev. Immunol.* 2:103-26 (1984).

Brown et al., "Human Melanoma-Associated Antigen p97 is Structurally and Functionally Related to Transferrin" *Nature* 296:171-173 (1982).

Rose et al., "Primary Structure of the Human Melanoma-Associated Antigen p97 (melanomatransferrin) deduced from the mRNA Sequence", *Proc. Nat. Acad. Sci (USA), 83:1261-1265 (1986).*

Ciocca et al., "Immunohistochemical Techniques Using Monoclonal Antibodies", *Meth. Enzymol.* 121:562-79 (1986).

Kimball (Ed.), Introduction to Immunology, (2nd Ed.), pp. 113-117, MacMillan Publ. Co. (1986).

Uotila et al., "Two-Site Sandwich Enzyme Immunoassay with Monoclonal Antibodies to Human Alpha-Fetoprotein" *J. Immunol. Meth.* 42:11 (1981).

Sikora, Monoclonal Antibodies, pp. 32-52 (Blackwell Scientific Publications, 1984).

Wensel and Meares, "'Bifunctional' Chelating Agents for Binding Metal Ions to Proteins" *Radio Immunoimaging and Radioimmunotherapy*, Elsevier, N.Y. (1983).

Colcher et al., "Use of Monoclonal Antibodies as Radiopharmaceuticals for the Localization of Human Carcinoma Xenografts in Athymic Mice", *Meth. Enzymol.*, 121:802-16 (1986).

Bradwell et al., "Developments in Antibody Imaging", in *Monoclonal Antibodies for Cancer Detection and Therapy*, Baldwin et al., (Eds), pp. 65-85 Academic Press (1985).

Arnon et al., "Monoclonal Antibodies for Immunotargeting of Drugs in Cancer Therapy" *Monoclonal Antibodies and Cancer Therapy*, Reisfeld et al., (Eds), pp. 243-56, Alan R. Liss, Inc. (1985).

Hellstrom et al., in *Controlled Drug Delivery* (2nd Ed.), Robinson et al., (Eds.) pp. 623-653, Marcel Dekker, Inc., (1987).

Thorpe, "Antibody Carriers of Cytotoxic Agents in Cancer Therapy: a Review", in *Monoclonal Antibodies '84: Biological and Clinical Applications*, Pinchera et al., (Eds.), pp. 475-506 (1985).

Thorpe et al., "The Preparation and Cytotoxic Properties of Antibody-Toxin Conjugates", *Immunol. Rev.* 62:119-58 (1982).

Senter et al., "Anti-Tumor Effects of Antibody-Alkaline Phosphatase Conjugates in Combination with Etoposide Phosphate", *Proc. Natl. Sci USA*, 85:4842-46 (1988).

Order, in Monoclonal Antibodies for Cancer Detection and Therapy, Baldwin (Ed.), pp. 303-316, Academic Press (1985).

Ramsey et al., "Bone Marrow Purging Using Monoclonal Antibodies", *J. Clin. Immunol.* 8(2):81-88 (1988).

Estin et al., "Recombinant Vaccinia Virus Vaccine Against the Human Melanoma Antigen p97 for use in Immunotherapy", *Proc. Natl. Acad. Sci. USA*, 85:1052 (1988).

Hu et al., "Characterization of a Recombinant Vaccinia Virus Expressing Human Melanoma-Associated Antigen p97", *J. Virol.* 62:176-180 (1988).

Douillard et al., "Enzyme-Linked Immunosorbent Assay for Screening Monoclonal Antibody Production using Enzyme-Labeled Second Antibody", *Meth. Enzymol.* 92:168-74 (1983).

Ey et al., "Isolation of Pure IgG1, IgG2a, and IgG2b, Immunoglobulins from Mouse Serum Using Protein A-Sepharose", *Immunochemistry* 15:429-436 (1978).

Sternberger, "The Unlabeled Antibody Peroxidase-Antiperoxidase (PAP) method", in *Immunochemistry*, pp. 104-69, John Wiley & Sons, New York, (1979).

Garrigues et al., "Detection of a Human Melanoma-Associated Antigen, p97, in Histological Sections of Primary Human Melanomas", *Int. J. Cancer*, 29:511-15 (1982).

Hellstrom et al., "Monoclonal Antibodies to Two Determinants of Melanoma-Antigen p97 Act Synergistically in Complement-Dependent Cytotoxicity", *J. Immunol.*, 127:157-60 (1981).

Hunkapiller et al., "Isolation of Microgram Quantities of Proteins from Polyacrylamide Gels for Amino Acid Sequence Analysis", *Methods in Enzymol*, 91:227-236 (1983). Laemmli, "Cleavage of Structural Proteins During the Assembly of the Head of Bacteriophage T4" *Nature*, 227:680-685 (1970).

Towbin et al., "Electrophoretic Transfer of Proteins from Polyacrylamide Gels to Nitro-Cellulose Sheets: Procedure and Some Applications", *Proc. Nat. Acad. Sci. USA* 76:4350-54 (1979).

Hawkes, "Identification of Concanaval in A-Binding Proteins After Sodium Dodecyl Sulfate-Gel Electrophoresis and Protein Blotting", *Anal. Biochem.* 123:143-146 (1982).

MONOCLONAL ANTIBODY TO NOVEL ANTIGEN ASSOCIATED WITH HUMAN TUMORS

FIELD OF THE INVENTION

The present invention relates to a novel monoclonal antibody and a novel antigen, and to methods for production and use of such novel monoclonal antibody reactive with human carcinoma cells. More specifically, the monoclonal antibody of this invention is reactive with the novel cell surface antigen, which is associated with a variety of human tumors including carcinomas of the breast, colon, ovary and lung, as well as melanomas and sarcomas.

The monoclonal antibody of this invention is suitable for both in vivo and in vitro clinical diagnostic purposes, such as the detection of malignant carcinomas. Additionally the antibody of the present invention is suited for therapeutic uses, for example to react with tumor cells, and in conjugates as a target-selective carrier of various agents which have anti-tumor effects including, but not limited to: chemotherapeutic drugs, toxins, immunological response modifiers, and radioisotopes. The antigen of the invention is also useful for therapeutic and diagnostic purposes.

BACKGROUND OF THE INVENTION

Carcinomas cause millions of deaths annually. For example, lung carcinomas are responsible for the majority of deaths from cancer among men and are overtaking breast carcinomas as the most frequent cause of cancer death among women. Most cases of carcinomas are incurable by chemotherapy and radiation therapy unless radically removed in the early stages of the disease. There is thus a great need for methods of diagnosis and therapy of carcinomas of the breast, colon, ovary and lung, as well as for other malignant neoplasms such as melanomas and sarcomas.

Monoclonal antibodies reactive with carcinoma-associated antigens are known (see, e.g., Papsidero, Semin. Surg. Oncol., 1 (4):171-81 (1985); Schlom et al., Important Adv. Oncol., 170-92 (1985); Allum et al., Surg. Ann., 18:41-64 (1986); Houghton et al., Semin. Oncol. 13 (2):165-79 (1986); Monoclonal Antibodies in Cancer: Advances for Diagnosis and Treatment, Roth (ed.), Futura Publishing, Mt. Kisco, New York (1986); and Cancer Diagnosis In Vitro Using Monoclonal Antibodies, Kupchik (ed.) Marcel Dekker, Inc., New York, (1988)).

Most of the known monoclonal antibodies are reactive with several types of human carcinomas, while a few antibodies react with carcinomas derived from specific organs of the body, e.g., lung, breast, ovary, colon, stomach or pancreas. The target antigens are commonly glycoproteins or glycolipids (see, e.g., Hellstrom et al., Cancer Research 46:3917-23 (1986); and Fink et al., Prog. Clin. Pathol., 9:121-33 (1984)). For example, monoclonal antibodies reactive with glycoprotein antigens on specific types of carcinomas include those described in U.S. Pat. No. 4,737,579 (monoclonal antibodies to non-small cell lung carcinomas), U.S. Pat. No. 4,753,894 (monoclonal antibodies to human breast cancer), U.S. Pat. No. 4,579,827 (monoclonal antibodies to human gastrointestinal cancer), and U.S. Pat. No. 4,713,352 (monoclonal antibodies to human renal carcinoma). Some monoclonal antibodies react with high molecular weight antigens which appear to be mucins. For example, monoclonal antibody B72.3 appears to recognize a tumor-associated oncofetal glycoprotein antigen of greater than 1,000 kd molecular weight that is selectively expressed on a number of different carcinomas. Thus, B72.3 has been shown to react with 84% of breast carcinomas, 94% of colon carcinomas, 100% of ovarian carcinomas and 96% of non-small-cell lung carcinomas (see Johnston, Acta Cytol., 1 (5):537-56 (1987) and U.S. Pat. No. 4,612,282, issued to Schlom et al.). Similarly, monoclonal antibody KC-4 recognizes an approximately 400-500 kd protein antigen expressed on a number of carcinomas, such as colon, prostate, lung and breast carcinoma (see U.S. Pat. No. 4,708,930).

Monoclonal antibodies reactive with glycolipid antigens that are believed to be associated with certain tumor cells have also been disclosed. For example, Young et al., J. Exo. Med., 150:1008-19 (1979) disclose the production of two monoclonal antibodies specific for asialo $GM_2$, a cell surface glycosphingolipid antigen that was established as a marker for BALB/c 3T3 cells transformed by Kirsten murine sarcoma virus. See, also, Kniep et al., J. Immunol., 131 (3):1591-94 (1983) and U.S. Pat. No. 4,507,391 (monoclonal antibody to human melanoma).

In addition, monoclonal antibodies reactive with glycolipid antigens found on specific types of carcinoma cells include those described by Rosen et al., Cancer Research. 44:2052-61 (1984) (monoclonal antibodies to human small cell lung cancer); Varki et al., Cancer Research, 44:681-87 (1984) (monoclonal antibodies to human adenocarcinomas of the lung, stomach and colon and melanoma), and U.S. Pat. No. 4,579,827 (monoclonal antibodies to human colon adenocarcinoma). See, also, Hellstrom et al., Proc. Nat'l. Acad. Sci. USA, 83:7059-63 (1986) which describes the L6 monoclonal antibody that recognizes a carbohydrate antigen expressed on the surface of human non-small cell lung carcinomas, breast carcinomas and colon carcinomas.

Additional monoclonal antibodies exhibiting a reactivity to antigens found on a variety of tumor cells are greatly needed. This is because of the antigenic heterogeneity of most tumors which often necessitates, in diagnosis or therapy, the use of a combination of different monoclonal antibodies directed to the same tumor mass. Furthermore, monoclonal antibodies that display a high degree of reactivity with a wide range of tumors, while showing the absence of or only a very weak reactivity with normal tissues, are not common. Such antibodies would clearly be advantageous.

It is thus apparent that a monoclonal antibody reactive with an antigen expressed at high levels by a variety of tumors may become useful towards an earlier diagnosis of cancers, a better definition of the spread of the cancer, the immunological monitoring of cancer patients, as well as for development of improved methods for therapy of cancers. It is also apparent that monoclonal antibodies to novel cell surface molecules can be used for further definition of such molecules which may be of value for preparing immunogens in the form of cancer vaccines, and which may also have important cellular functions, for example, as receptors of hormones or growth factors or as molecules otherwise involved in intra- and intercellular communication. The antigens may even have enzymatic or growth factor activity by themselves.

SUMMARY OF THE INVENTION

The present invention provides such a monoclonal antibody, L45, which is specific for a determinant site on a cell surface glycoprotein antigen, the L45 antigen, associated with a variety of human tumor cells, including lung, breast, ovary and colon carcinoma and melanoma and sarcoma cells. Thus, the antibody of the invention can be useful for the diagnosis and therapy of tumors expressing the L45 antigen identified by antibody L45. The L45 antibody of the invention is of the class IgG, and IgG2a subclass and shows no significant reactivity with normal human cells.

The antibody of the invention may be used in in vitro diagnostic methods for determining the presence of a malignant condition in human lung tissue and other human tissues. The methods involve examining the tissue for the presence of an antigen having the characteristics of the 100,000 dalton L45 antigen glycoprotein reactive with antibody L45. For example, the tissue can be contacted with the L45 monoclonal antibody of the invention which defines a determinant site on a cell-associated antigen having the characteristics of the L45 antigen, a functional equivalent or a fragment of this antibody and any interactions of said antibody and antigenic determinants are detected. One such method involves the determination of the presence of carcinoma cells in a specimen suspected of containing such cells. The specimen is contacted with the monoclonal antibody, which is capable of distinguishing such cells from other cell types which may be present in the specimen. The contact is carried out under conditions for binding of the antibody to such cells. After contact, the presence or absence of binding of the antibody to the cells in the specimen is determined. This binding is related to the presence or absence of carcinoma cells in the specimen. Generally, the specimen is contacted with a labeled specific binding partner of the monoclonal antibody. This label is capable of producing a detectable signal. Alternatively, the monochronal antibody itself may be labeled.

Another diagnostic method involves the in vivo localization of a tumor by administering to a patient a purified antibody or antibody fragment of the present invention labeled with an agent which gives a detectable signal. The localization is then detected using external scintography, emission tomography or radionuclear scanning. This method can also provide better ways to stage cancer patients with respect to the extent of disease and to monitor changes in response to therapy.

The invention also has therapeutic applications, since the L45 antibody and similar antibodies can react with the L45 antigen that is expressed in high concentrations at the tumor cell surface. The monoclonal antibody of the invention may be used to prepare a composition for treating tumors. The composition comprises a therapeutically effective amount of the antibody in association with a pharmaceutically acceptable parenteral vehicle. The antibody of the invention can also be used in immunoconjugates as a carrier of various agents which have an antitumor effect, including, but not restricted to, chemotherapeutic drugs, toxins, immunological response modifiers, and radioisotopes.

The invention also comprises the novel L45 antigen characterized by a molecular weight of about 100,000 daltons and having an amino terminal amino acid sequence: S-A-Y-G-D-T-I-I-I-P-X-R-L-D-V-P-Q-N-L-M-F, in which X represents an unidentified amino acid, and equivalents, identified by antibody L45 and the class of antibodies that bind to this antigen.

The invention includes methods for using the purified or cloned L45 antigen as a vaccine to immunize against certain tumors.

DETAILED DESCRIPTION OF INVENTION

In order that the invention herein described may be more fully understood, the following detailed description is set forth.

The present invention concerns a novel monoclonal antibody, designated L45, which is specifically reactive with an antigen (L45 antigen) localized on human tumor cells including carcinomas of the lung, colon, breast, ovary, and melanoma and sarcoxa cells, methods for producing the L45 monoclonal antibody and diagnostic and therapeutic methods employing the antibody. The L45 antibody reacts with a range of tumors while showing essentially no reactivity with normal human tissues or other types of tumors such as lymphomas.

The invention further concerns a novel cell surface glycoprotein antigen, designated L45 antigen, associated with human tumors of the lung, breast, colon, ovary, and melanomas and sarcomas and methods for using the L45 antigen.

The monoclonal antibody of the invention can be prepared by hybridoma fusion techniques or by techniques that utilize EBV-immortalization technologies.

Hybridoma fusion techniques were first introduced by Kohler and Milstein (see, Kohler and Milstein, *Nature*, 256:495-97 (1975); Brown et al., *J. Immunol.*, 127 (2):539-46 (1981); Brown et al., *J. Biol. Chem.*, 255:4980-83 (1980); Yeh et al., *Proc. Nat'l. Acad. Sci.* (USA), 76 (6):2927-31 (1976); and Yeh et al., *Int. J. Cancer*, 29:269-75 (1982)).

These techniques involve the injection of an immunogen (e.g., purified antigen or cells or cellular extracts carrying the antigen) into an animal (e.g., a mouse) so as to elicit a desired immune response (i.e., production of antibodies) in that animal. For example, human lung carcinoma cells from pleural effusions, cultured cells from explanted human non-small cell lung carcinomas (NSCLC), or cells from a normal fetal lung or lysates from such cells may be used as the immunogen. In the illustrative example herein, explanted cells from a NSCLC (human lung adenocarcinoma), line CH3, were used as the immunogen. The cells are injected, for example, into a mouse and, after a sufficient time, the mouse is sacrificed and somatic antibody-producing lymphocytes are obtained. Antibody-producing cells may be derived from the lymph nodes, spleens and peripheral blood of primed animals. Spleen cells are preferred. Mouse lymphocytes give a higher percentage of stable fusions with the mouse myelomas described below. The use of rat, rabbit and frog somatic cells is also possible. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al., in *Monoclonal Hybridoma Antibodies: Techniques And Applications*, Hurell (ed.) pp. 51-52 (CRC Press 1982)). Hybridomas produced according to these methods can be propagated in vitro or in vivo (in ascites fluid) using techniques known in the art (see, generally, Fink et al., supra. at page 123, FIG. 6-1).

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. As discussed by Cole et al., supra, when human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies (see Cole et al., supra).

For certain therapeutic applications chimeric (mouse-human) or human monoclonal antibodies may be preferable to murine antibodies, because patients treated with mouse antibodies generate human antimouse antibodies. (Shawler et al., *J. Immunol.* 135:1530-35 (1985)). Chimeric mouse-human monoclonal antibodies reactive with the L45 antigen can be produced, for example, by techniques recently developed for the production of chimeric antibodies (Oi et al., *Biotechnologies* 4(3):214-221 (1986); Liu et al., *Proc. Nat'l. Acad. Sci.* (*USA*) 84:3439-43 (1987)). Accordingly, genes coding for the constant regions of the murine L45 antibody molecule are substituted with human genes coding for the constant regions cf an antibody with appropriate biological activity (such as the ability to activate human complement and mediate ADCC). Novel antibodies of mouse or human origin, can be also made to the L45 antigen having the appropriate biological functions. For example, human monoclonal antibodies may be made by using the antigen, e.g. the L45 antigen of the invention, to sensitize human lymphocytes to the antigen in vitro followed by EBV-transformation or hybridization of the antigen-sensitized lymphocytes with mouse or human lymphocytes, as described by Borrebaeck et al. (*Proc. Nat'l. Acad. Sci.* (*USA*)) 85:3995-99 (1988)).

According to a preferred embodiment, the antibody of this invention, designated L45, was produced via hybridoma techniques using a lung adenocarcinoma cell line CH3 as the immunogen as described in the Example, infra. The L45 hybridoma, producing the L45 antibody, has been deposited on Aug. 25, 1988 with the American Type Culture Collection ATCC 12301 Parklawn Drive, Rockville, Md., and has there been identified as follows:

| L45 | Accession No.: | HB 9804 |

The L45 antibody is of the IgG2a subclass. The antibody displays a very strong reactivity with tumor cells of a variety of types, for example, carcinomas of the breast, lung, colon and ovary, as well as with malignant melanomas and sarcomas. The L45 antibody shows no detectable binding to the cell lymphoma cell lines, CEM, MOLT-4, and the B cell lymphoma line P3HR-1.

In addition, the antibody of this invention does not display any immunohistologically detectatle binding to normal human tissues such as fibroblasts, endothelial cells or epithelial cells from the major organs, e.g., kidney, spleen, liver, skin, lung, breast, colon, brain, thyroid, heart, lymph nodes or ovary. Nor does the antibody react with peripheral blood leukocytes. Thus, this antibody is superior to most known antitumor antibodies in its specificity for a range of tumor cells and in its high degree of specificity for tumor cells as compared to normal cells (see, e.g., Hellstrom et al., *Covalently Modified Antigens And Antibodies In Diagnosis And Therapy*, Quash/Rodwell (eds.), pp. 24-28 (Marcel Dekker, Inc., (1989); and Bagshawe, *Br. J. Cancer*, 48:167-75 (1983)).

It should be understood that the present invention encompasses the L45 antibody described above and any fragments thereof containing the active binding region of the antibody, such as Fab, F(ab')$_2$ and Fv fragments. Such fragments can be produced from the L45 antibody using techniques well established in the art (see, e.g., Rousseaux et al., in *Methods Enzymol.*, 121:663-69 Academic Press, (1986)).

In addition, the present invention encompasses antibodies that are capable of binding to the same antigenic determinant as the L45 antibody and competing with the L45 antibody for binding at that site. These include antibodies having the same antigenic specificity as the L45 antibody but differing in species origin, isotype, binding affinity or biological functions (e.g., cytotoxicity). For example, class, isotype and other variants of the antibody of the invention may be constructed using recombinant class-switching and fusion techniques known in the art (see, e.g., Thammana et al., *Eur. J. Immunol.*, 13:614 (1983); Spira et al., *J. Immunol. Meth.*, 74:307-15 (1984); Neuberger et al., *Nature*, 312:604-08 (1984); and Oi et al., supra)). Thus, chimeric antibodies or other recombinant antibodies (e.g., antibody fused to a second protein such as a lymphokine) having the same binding specificity as the L45 antibody fall within the scope of this invention. Furthermore, since the L45 antigen to which the antibody of the invention binds is a novel pan-tumor antigen, the antibody of the invention includes antibodies that bind to any antigenic determinant on that L45 antigen, including determinants other than that with which the L45 antibody reacts.

Also included within the scope of the invention are anti-idiotypic antibodies of the L45 antibody of the invention. These anti-idiotypic antibodies can be produced using the L45 antibody as immunogen and are useful for diagnostic purposes in detecting humoral response to tumors and in therapeutic applications, e.g., in a vaccine, to induce an anti-tumor response in patients (see, e.g., Nepom et al., *Cancer And Metastasis Reviews,* 6:487-501 (1987); and Lee et al., *Proc. Nat'l. Acad. Sci. (USA),* 82:6286-90 (1985)).

The L45 antibody can be used to isolate and characterize the L45 antigen to which it binds. Thus, L45 can be used as a probe to identify and characterize the epitope recognized by the antibody and to further define the L45 antigen on the surface of the carcinoma cells (see, e.g., Hakomori, *Ann. Rev. Immunol.,* 2:103-26 (1984); Brown et al., *J. Immunol.,* 127: 539-546 (1981); Brown et al., *Nature,* 296: 171-173 (1982); and Rose et al.; *Proc. Nat'l. Acad. Sci. (USA),* 83: 1261-1265 (1986)).

The L45 antigen recognized by the monoclonal antibodies of the present invention comprises a novel cell surface glycoprotein antigen characteristic of tumor cells including carcinomas of the breast, colon, ovary and lung as well as melanomas and sarcomas. L45 antigen has a molecular weight of about 100,000 daltons when subjected to immunoprecipitation on polyacrylamide gel electrophoresis.

The amino terminal amino acid sequence of the novel L45 glycoprotein antigen is as follows:

```
1             5            10
W—Y—T—V—N—S—A—Y—G—D—T—I—I—I—

15           20           25
     —P—X—R—L—D—V—P—Q—N—L—M—F
``` in which X represents an amino acid that has not been identified as yet, and the rest of the letters represent the conventional single letter abbreviations for amino acids. A comparison of the 26 residue L45 amino-terminal sequence with those stored in the current protein data base (PIR Release 16, March 1988) reveals no significant sequence homology with any other known sequences.

The monoclonal antibody of the invention is also useful for diagnostic applications, both in vitro and in vivo, for the detection of human tumors carrying the L45 antigen with which the L45 antibody is specifically reactive. In vitro diagnostic methods are well known in the art (see, e.g., Roth, supra, and Kupchik, supra), and include immunohistological detection of tumor cells (e.g., on human tissue, cells or excised tumor specimens) or serologic detection of tumor-associated antigens (e.g., in blood samples or other biological fluids).

Immunohistological techniques involve contacting a biological specimen such as a tumor tissue specimen with the antibody of the invention and then detecting the presence on the specimen of the antibody complexed to its antigen. The formation of such antibody-antigen complexes with the specimen indicates the presence of tumor cells in the tissue. Detection of the antibody on the specimen can be accomplished using techniques known in the art such as the immunoperoxidase staining technique, the avidin-biotin (ABC) technique or immunofluorescence techniques (see, e.g., Ciocca et al., *Meth. Enzymol.* 121:562-79 (1986); Hellstrom et al., *Cancer Research,* 46:3917-23 (1986); and Kimball (ed.), *Introduction To Immunology* (2nd Ed.), pp. 113-117, Macmillan Publ. Co., (1986)). For example, immunoperoxidase staining was used as described in Example III, infra, to demonstrate the reactivity of the L45 antibody with lung, breast, colon, and ovary carcinomas and melanomas and sarcomas, and the lack of reactivity of the antibody with normal human tissue specimens.

Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample (see, e.g., Uotila et al., *J. Immunol. Methods,* 42:11 (1981) and Allum et al., supra. at pp. 48-51). These assays, using the L45 antibody disclosed herein, can therefore be used for the detection in biological fluids of the L45 antigen with which the L45 antibody reacts and thus the detection of various carcinomas and melanomas in human patients. Thus, it is apparent from the foregoing that the L45 antibody of the invention can be used in most assays involving antigen-antibody reactions. These assays include, but are not limited to, standard RIA techniques, both liquid and solid phase, as well as ELISA assays procedures, immunofluorescence techniques, and other immunocytochemical assays (see, e.g., Sikora et al. (eds.), *Monoclonal Antibodies,* pp. 32-52, Blackwell Scientific Publications, (1984)).

The L45 antibody of the invention is also useful for in vivo diagnostic applications for the detection of human tumors. One such approach involves the detection of tumors in vivo by tumor imaging techniques using the antibody labeled with an appropriate imaging reagent that produces detectable signal. Imaging reagents and procedures for labeling antibodies with such reagents are well known (see, e.g., Wensel and Meares, *Radio Immunoimaging and Radioimmunotherapy,* Esevier, N.Y. (1983); Colcher et al., *Meth. Enzymol.,* 121:802-16 (1986)). The labeled antibody may be detected by a technique such as radionuclear scanning (see, e.g., Bradwell et al. in *Monoclonal Antibodies for Cancer Detection and Therapy,* Baldwin et al. (eds.), pp. 65-85, Academic Press (1985)).

The L45 antibody of the invention has a number of in vivo therapeutic applications. In addition to being used alone to target tumor cells, the antibody can be used in conjunction with an appropriate therapeutic agent to treat human cancer. For example, the antibody can be conjugated or linked to a therapeutic drug or toxin for delivery of the therapeutic agent to the site of the cancer. Techniques for conjugating such therapeutic agents to antibodies are well known (see, e.g., Arnon et al., *Monoclonal Antibodies And Cancer Therapy,* Reisfeld et al. (eds.), pp. 243-56, Alan R. Liss, Inc., (1985); Hellstrom et al., in *Controlled Drug Delivery* (2nd ed.), Robinson et al. (eds.), pp. 623-53, Marcel Dekker, Inc., (1987); Thorpe, *Monoclonal Antibodies '84: Biological And Clinical Applications,* Pinchera et al. (eds.), pp. 475-506 (1985); and Thorpe et al., *Immunol. Rev.,* 62:119-58 (1982)). Since the L45 antibody is not easily internalized when cells are exposed to it in vitro, it may be preferable to target chemotherapeutic drugs to the tumor cells by coupling the antibody with an enzyme, e.g., using recombinant DNA techniques. When such conjugates are localized to the tumor, the enzyme can convert an inactive (nontoxic) prodrug which is administered after the conjugates have bound to the tumor cells, to an active anticancer drug. (See, e.g., Senter et al., *Proc. Nat'l Acad. Sci. (USA)*, 85:4842-46 (1988)).

Alternatively, the antibody can be coupled to a source of high-energy radiation, e.g., a radioisotope such as $^{131}$I, which, when localized at the tumor site, results in a killing of several cell diameters (see, e.g., Order, in *Monoclonal Antibodies For Cancer Detection And Therapy*, Baldwin et al. (eds.), pp. 303-16 Academic Press, (1985)). According to yet another embodiment, the L45 can be conjugated to a second antibody to form an antibody heteroconjugate for the treatment of tumor cells as described by Segal in U.S. Pat. No. 4,676,980.

Still other therapeutic applications for the L45 antibody of the invention include its use, either in the presence of complement or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient (see, e.g., Ramsay et al., *J. Clin. Immunol.*, 8(2):81-88 (1988)).

Furthermore, chimeric or other recombinant L45 antibodies of the invention, as described earlier, may be used therapeutically. For example, a fusion protein comprising at least the antigen-binding region of the L45 antibody joined to at least a functionally active portion of a second protein having anti-tumor activity, e.g., a lymphokine or oncostatin, may be used to treat human tumors in vivo. In addition, a chimeric L45 antibody wherein the antigen-binding region of L45 is joined to a human Fc region, e.g., IgGl, may be used to promote antibody-dependent cellular cytotoxicity or complement mediated cytotoxicity. Furthermore, recombinant techniques known in the art can be used to construct bispecific antibodies wherein one of the binding specificities of the antibody is that: of L45 (see, e.g., U.S. Pat. No. 4,474,893).

Finally, anti-idiotypic antibodies of the L45 antibody may be used therapeutically in active tumor immunization and tumor therapy (see, e.g., Hellstrom et al., "Immunological Approaches To Tumor Therapy Monoclonal Antibodies, Tumor Vaccines, And Anti-Idiotypes", in *Covalently Modified Antigens And Antibodies In Diagnosis And Therapy*, supra, at pp. 35-41).

It is apparent therefore that the present invention encompasses pharmaceutical compositions, combinations and methods for treating human tumors. For example, the invention includes pharmaceutical compositions for use in the treatment of human tumors comprising a pharmaceutically effective amount of a L45 antibody and a pharmaceutically acceptable carrier. The compositions may contain the L45 antibody, either unmodified, conjugated to a therapeutic agent (e.g., drug, toxin, enzyme or second antibody) or in a recombinant form (e.g., chimeric or bispecific L45). The compositions may additionally include other antibodies or conjugates for treating carcinomas (e.g., an antibody cocktail).

The antibody compositions of the invention can be administered using conventional modes of administration including, but not limited to, intravenous, intraperitoneal, oral, intralymphatic or administration directly into the tumor. Intravenous administration is preferred.

The antibody compositions of the invention may be in a variety of dosage forms which include, tut are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The antibody compositions also preferably include conventional pharmaceutically acceptable carriers and adjuvants known in the art such as human serrum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient. Nevertheless, an effective dose of the antibody compositions of this invention may be in the range of from about 1 to about 5000 mg/m$^2$.

The novel antigen of the present invention, referred to as antigen L45 may also be used for therapeutic applications. The antigen can be purified from tumors or produced by recombinant DNA technology (Brown et al., copending U.S. patent application Ser. No. 827,313, filed on Feb. 7, 1986, incorporated by reference herein). The gene coding for the L45 antigen may be cloned by methods which first enrich the mRNA of the L45 antigen. By one such method, polysomes (consisting of mRNA ribosomes and nascent polypeptide chains) can be purified by immunoaffinity chromatography with antibody that recognizes the L45 antigenic determinant on the nascent chain. The mRNA is isolated by immunoprecipitation with, e.g., L45 antibody and the cDNA is cloned in an appropriate expression vector. Alternatively, L45 antibody or antiserum to L45 antigen might be used to screen a cDNA library using an expression vector. The purified or cloned L45 antigen may be administered alone as an immunogen or together with a proper immunological adjuvant.

Purified or cloned L45 antigen may be used in the methods of the invention as a vaccine to immunize against certain tumors. Procedures for preparing such vaccines are known in the art (see, e.g., Estin et al., *Proc. Nat'l. Acad. Sci. (USA)*, 85:1052 (1988)). Briefly, recombinant viruses are constructed for expression of the cloned tumor-associated antigen, for example L45 antigen. Cells infected with the recombinant viruses will express the tumor antigen at the surface of the cells together with the host's incompatibility antigens and immunogenic viral proteins. This favors the induction of cellular immunity which plays a key role in tumor rejection. A suitable virus, for example vaccinia virus derived from a plaque-purified virus of the Wyeth smallpox vaccine (New York City Board of Health strain), is used to construct a recombinant virus containing the coding sequence of the L45 antigen under control of the vaccinia virus "7.5 K" promoter (Hu et al., *J. Virol.* 62:176-180 (1988)). The recombinant virus may then be administered intravenously as a vaccine to protect against cancer.

In order that the invention described herein may be more fully understood, the following examples are set forth. It should be understood that these examples are for illustrative purposes only and are not to be construed as limiting the scope of this invention in any manner.

EXAMPLE I

Preparation of the L · Monoclonal Antibody

The L45 monoclonal antibody of the invention was produced using hybridoma fusion techniques described previously by Yeh et al., *Proc. Nat'l Acad. Sci. (USA)* (1979), supra). Briefly, a three month-old BALB/c mouse was immunized using explanted cultured cells from a human adenocarcinoma of the lung, designated CH3, as the immunogen. The mouse received six (6) intraperitoneal (i.p.) injections and approximately $10^7$ cells for each immunization. Three days after the last immunization, the spleen was removed, and the spleen cells were suspended in culture medium. The spleen cells were then fused with transfected NS1 mouse myeloma cells with geniticin (Kohler and Milstein, supra), using polyethylene glycol (PEG), and the cell suspension grown in microtiter wells in selective HAT medium as described by Yeh et al., *Proc Nat's. Acad. Sci. (USA)*, supra. The mixture was seeded to form low density cultures originating from single fused cells or clones.

The supernatants from these hybridoma cultures were then screened for direct binding activity on the lung cancer cell line, CH3, and against short-term cultures of human fibroblasts using an ELISA assay similar to that described by Douillard et al., *Meth. Enzymol.*, 92:168–74 (1983). According to this assay, the antigen (with which the antibody being screened for is reactive) is immobilized on microtiter plates and then incubated with hybridoma supernatants. If a supernatant contains the desired antibody, the antibody will bind to the immobilized antigen and is detected by addition of an anti-immunoglobulin antibody-enzyme conjugate and a substrate for the enzyme which leads to a measurable change in optical density.

For this example, lung cancer cells or control fibroblast cells or peripheral blood leukocytes (PBLs) were dispensed into a 96-well tissue culture plate (Costar, Cambridge, Mass.) and incubated overnight in a humid 37° C. incubator (5% $CO_2$). The cells were then fixed with 100 µl of freshly prepared 1.0% glutaraldehyde to a final well concentration of 0.5% and incubated for 15 min at room temperature, followed by washing three times with 1 X PBS. The cells were next blocked for 30 min with 5% BSA in PBS and washed again three times with PBS. The supernatants from the hybridoma cultures were then added at 100 µl/well, the wells incubated for 1 hr at room temperature, and the cells washed three times with PBS. Next, goat anti-mouse horseradish peroxidase (Zymed, CA) diluted in 0.1% BSA and PBS was added to a concentratior of 100 µl/well. The reaction mixture was incubated for either 1 hr at room temperature or 30 min at 37° C. and the cells were then washed three times with PBS. o-phenylenediamine (OPD) was then added at 100 µl/well and the plates incubated in the dark at room temperature for 5–45 min. Antibody binding to the cells was detected by a color change in the wells that occurred within 10–20 min. The reaction was stopped by adding 100 µl/well $H_2SO_4$ and the absorbance read in a Dynatech (Alexandria, Va.) Microelisa autoreader at 492 nm.

The wells still positive on immunizing cell lines and negative on PBLs were tested by immunohistology technologies on immunizing cell line pellets and normal kidney, liver, and spleen tissues.

It should be noted that this assay can be performed using intact cells or purified soluble antigen or cellular extracts as the immobilized antigen. When soluble antigen or cell extracts were used as antigen, the antigen was initially plated at 50 µl/well in PBS and the plates were incubated overnight at room temperature before beginning the assay. When using intact cells as antigen, they may be used fresh or after fixation. In either case, the cells were initially plated at $10^4$ cells at 100 µl/well in culture medium and incubated overnight in a 37° C. incubator (5% $CO_2$).

Hybridomas which produced antibodies birding to the lung cancer cell line and not to the normal tissues were thus selected, cloned, expanded in vitro, and further tested for antibody specificity. Those hybridomas which produced antibody reactive with human lung cancer were recloned, expanded, and injected into pristane-primed 3-month old BALB/c mice, where they grew as ascites tumors.

Following this procedure, hybridoma cell line L45 was obtained, cloned and injected into mice to develop as an ascites tumor. As disclosed above, the L45 hybridoma has been deposited with the ATCC. Antibody secreted into the ascites was purified on protein A-Sepharose (see, e.g., Ey et al., *Immunochemistry*, 15:429–436 (1978)) or by gel filtration on Sephacryl S-300. Purified L45 antibody was used for further characterization.

EXAMPLE II

Characterization of The L45 Monoclonal Antibody Isotype Determination

To determine the class of immunoglobulin produced by the L45 hybridoma, the following techniques were utilized:

a) Ouchterlony immunodiffusion

An aliquot of supernatant of the L45 hybridoma cells was placed into the center well of a 25% agar plate. Monospecific rabbit anti-mouse Ig isotypes antibodies (Southern Biotechnology, Birmingham, Ala.) were placed in the outer wells and the plate was incubated for 24–48 hr at 37° C. Precipitation lines were then read.

b) ELISA isotyping

Dynatech Immulon 96-well plates were coated with goat anti-mouse Ig antibodies at 1 µg/ml concentration, 50 µl/well in PBS and left covered overnight at 4° C. The plates were washed with PBS/Tween 20, 0.05% and blocked with medium 100 µl/well for 1 hr at room temperature. After washing the plates, supernatants from the L45 hybridoma were added and incubated at room temperature for 1 hr. After washing with PBS containing bovine serum albumin (BSA) plates were incubated at 37° C. for 2 hr with monospecific rabbit anti-mouse Ig isotype antibodies coupled to peroxidase (Zymed). After washing, plates were incubated with 1 mg/ml o-phenylenediamine and 0.03% $H_2O_2$ in 0.1 M citrate buffer, pH 4.5. Optical density at 630 nm was determined on a Dynatec ELISA plate reader.

Based on these procedures, it was determined that the L45 monoclonal antibody is of the IgG2*a* isotype.

Binding Characteristics of The L45 Monoclonal Antibody

The subcellular localization of antigen was determined by measuring antibody binding to cells before or after permeabilization with non-ionic detergent. Antibodies binding to the cell surface of intact cultured cells were identified by direct fluorescence using the fluorescence activated cell sorter (FACS) II, as described by Hellstrom et al., Cancer Research 46:3817-3923 (1986). Briefly for binding analyses using a FACS cell sorter, $1 \times 10^6$ cultured cells were aliquoted in 15% fetal bovine serum (FBS) in IMDM media (Gibco, Grand Island, N.Y.) to a total volume of 500 μl/tube. The cells were centrifuged for 1.5 min on a Serofuge and the supernatant removed. 100 μl of the L45 monoclonal antibody at 10 μg/ml was added to each tube, the contents of which was then mixed and incubated on ice for 30 min. The reaction mixture was washed three times with 500 μl of 15% FBS/IMDM by centrifugation for 1.5 min on the Serofuge (tubes were blotted after the third wash). Then, 50 μl of optimized FITC-conjugated goat anti-mouse IgG antibody (Tago, Burlingame, CA) diluted 1:25 in 15% FBS/IMDM was added to each tube and the reaction mixture was mixed and incubated for 30 min. The wash step was then repeated and after blotting of the tubes, each pellet was resuspended in 200-500 μl of PBS. Each sample was run on a Coulter Epics C FACS and the mean fluorescence intensity (MFI) was determined. From the MFI, the linear fluorecent equivalent (LFE) was determined. The LFE of each test sample divided by the LFE of a negative control gave a ratio between the brightness of cells stained by specific vs. control antibody (1.0 = no difference in fluoresence, 2.0 = fluoresence twice as bright, etc.). The binding data is shown in Table 1 below.

TABLE 1

Binding of L45 Antibody to Various Cell Lines

| Cell Lines | L45 Antibody Binding Ratio |
| --- | --- |
| 2981 Lung carcinoma (ca.) | 15.6 |
| CH3 lung ca. | 3.3 |
| 2707 lung ca. | 1.0 |
| HCT116 lung ca. | 7.4 |
| 3477 breast ca. | 13.5 |
| RCA colon ca. | 21.0 |
| 3347 breast ca. | 1.6 |
| C colon ca. | 24.3 |
| CEM T lymphocytes | 1.0 |
| MOLT 4 T lympocytes | 1.3 |
| P34R-1 B lymphoma | 1.0 |
| Peripheral blood cells | 1.0 |

As Table 1 demonstrates, the L45 monoclonal antibody reacted with lung, breast and colon carcinoma cell lines, but did not react with T or B lyphoma lines nor with normal peripheral blood leukocytes.

Immunohistology

The PAP technique of L. A. Sternberger as described in Immunochemistry, pp. 104-69, John Wiley & Sons, New York (1979), as modified by Garrigues et al., Int. J. Cancer, 29:511-15 (1982), was used for immunohistological studies on frozen tissue sections. The target tissues for these tests were obtained at surgery and frozen within 4 hr of removal using isopentane precooled in liquid nitrogen. Tissues were then stored in liquid nitrogen or at −70° C. until used. Frozen sections were prepared, air-dried, treated with acetone and dried again (see Garrigues et al., supra). Sections to be used for histologic evaluation were stained with hematoxylin. To decrease non-specific backgrounds, sections were preincubated with normal human serum diluted 1/5 in PBS (see Garrigues et al., supra). Mouse antibodies, rabbit anti-mouse IgG, and mouse PAP were diluted in a solution of 10% normal human serum and 3% rabbit serum. Rabbit anti-mouse IgG (Sternberger-Meyer Immunochemicals, Inc., Jarettsville, Md.) was used at a dilution of 1/50. Mouse peroxidase-antiperoxidase complexes (PAP, Sternberger-Meyer Immunochemicals, Inc.) containing 2 mg/ml of specifically purified PAP were used at a dilution of 1/80.

The staining procedure consisted of treating serial sections with either specific antibody, i.e., L45, or a control antibody for 2.5 hr, incubating the sections for 30 min at room temperature with rabbit anti-mouse IgG diluted 1/50 and then exposing the sections to mouse PAP complexes diluted 1/80 for 30 min at room temperature. After each treatment with antibody, the slides were washed twice in PBS.

The immunohistochemical reaction was developed by adding freshly prepared 0.5% 3,3'-diaminobenzidine tetrahydrochloride (Sigma Chemical Co., St. Louis, Mo.) and 0.01% $H_2O_2$ in 0.05 M Tris buffer, pH 7.6, for 8 min (see Hellstrom et al., J. Immunol., 127:57-60 (1981)). Further exposure to a 1% $OsO_4$ solution in distilled water for 20 min intensified the stain. The sections were rinsed with water, dehydrated in alcohol, cleared in xylene, and mounted on slides. Parallel sections were stained with hematoxylin.

The slides were each evaluated under code and coded samples were checked by an independent investigator. Typical slides were photographed by using differential interference contrast optics (Zeiss-Nomarski). The degree of antibody staining was evaluated as 0 (no reactivity), + (a few weakly positive cells), + + (at least one third of the cells positive), + + + (most cells positive), + + + + (all cells strongly positive). Because differences between + and 0 staining were less clear cut than between + and + + staining, a staining graded as + + or greater was considered "positive". Both neoplastic and stroma cells were observed in tumor samples. The staining recorded is that of the tumor cells because the stroma cells were not stained at all or were stained much more weakly than the tumor cells.

Table 2 below presents the immunohistological staining of various tumor and normal tissue specimens using the L45 monoclonal antibody. As the table clearly demonstrates, the L45 antibody reacts with a wide range of human tumor specimens, and shows no reactivity with any of the number of normal human tissues tested.

TABLE 2

Immunoperoxidase Staining of Tumors and Normal Tissue Specimens with L45 Monoclonal Antibody

| Tissue Type | Antibody Binding (Number of Positive Tumors/ Total Number of Tumors Tested) |
| --- | --- |
| CA. COLON | 13/13 |
| CA. LUNG | 10/13 |
| CA. BREAST | 15/15 |
| CA. OVARIAN | 5/6 |
| MELANOMA | 8/8 |
| SARCOMA | 4/6 |
| Normal Tissues: | |
| SPLEEN | 0/3 |
| KIDNEY | 0/4 |
| LIVER | 0/4 |
| HEART | 0/1 |
| OVARY | 0/1 |
| ADRENAL | 0/1 |
| TESTIS | 0/1 |
| BREAST | 0/8 |
| TONSIL | 0/1 |
| SKIN | 0/5 |
| LUNG | 0/5 |
| COLON | 0/6 |

TABLE 2-continued

Immunoperoxidase Staining of Tumors and Normal
Tissue Specimens with L45 Monoclonal Antibody

| Tissue Type | Antibody Binding (Number of Positive Tumors/ Total Number of Tumors Tested) |
|---|---|
| BRAIN | 0/2 |
| THYROID | 0/3 |
| LYMPH NODES | 0/2 |

EXAMPLE III

L45 Antigen Recognized By L45 Antibody

Purification

In order to characterize the antigen reactive with the L45 antibody, L45 antigen was isolated from A549 cells (ATCC, Rockville, Md.) and purified by immunoaffinity chromatography. L45 antigen was solubilized from A549 cell membranes with 0.5% NP40 in 10 mM Tris-HCl buffer, pH 8.5, containing 0.15 M NaCl and 1 mM. phenylmethane-sulfonylfluoride and purified by immunoaffinity chromatography. The column was prepared by coupling L45 antibody to carbonyl-diimidazole-activated agarose (Reacti-Gel (6X), Pierce, Rockford, Ill.). Bound L45 antigen was reluted from the affinity support with 0.5 M glycine-HCl buffer, pH 2.3, containing 0.5% NP40 and 0.15 M NaCl. Eluted L45 antigen was further purified by preparative sodium dodecylsulfate polyacrylamide gel electrophoresis (SDS-PAGE) on a 15% acrylamide gel. Following electrophoresis, the gel was stained with Coomassie Brilliant Blue, 0.5% by weight in 10% acetic acid and 30% isopropanol) and destained in a solution of acetic acid (5%, v:v) and methanol (17%, v:v). The stained L45 antigen band (Mr 100,000) was excised with a razor blade and immediately subjected to electroelution with a ECU-040 Electroeluter/Concentrator (C.B.S. Scientific Co., San Diego, Calif.), as described by Hunkapiller, et al., *Methods in Enzymology* 91:227-236 (1983)).

Sequence Analysis

Automated Edman degradation was performed with two preparations of L45 antigen: 1) 36 pmol of antigen and 2) 14 pmol of antigen in a pulsed liquid protein sequencer (Model 475A, Applied Biosystems, Inc., Foster City, Calif.). The phenylthiohydantoin amino acid derivatives were analyzed by reversed-phase high performance liquid chromatography (HPLC) on-line on a Model 120A on-line HPLC unit (Applied Biosystems, Inc.) using a PTH C18 column and a sodium acetate/tetrahydrofuran/acetonitrile gradient for elution.

The amino-terminal amino sequence of L45 antigen is as follows:

```
1           5            10
W—Y—T—V—N—S—A—Y—G—D—T—I—I—I—

15          20         25
    —P—X—R—L—D—V—P—Q—N—L—M—F
``` in which X represents an amino acid that has not been identified.

A comparison of the 26-residue L45 amino-terminal sequence against the PIR database (PIR Release 180, September, 1988; GenBank Release 57.0, September, 1988; NEW, Nov. 30, 1988; DIF, Nov. 30, 1988; SWISS PROT, Nov. 30, 1988; and LOSPRO, Nov. 30, 1988) did not reveal significant sequence homology with any other known sequence.

The antigen recognized by the L45 antibody is a protein antigen of about 100,000 daltons molecular weight (Mr).

Immunological Characterization

A) Western Blot Analysis

Immunoaffinity-purified L45 antigen was subjected to SDS-PAGE (7.5% acrylamide, Mini-Protean II Electrophoresis Cell, Bio-Rad, Richmond, Calif.), as described by Laemmli, U.K., *Nature* 227:680-685 (1970), and electrophoretically transferred (Mini Trans-Blot Electric Transfer Cell, Bio-Rad, Richmond, Calif.) to Hybond-N nylon membrane (Amersham Corp., Arlington Heights, Ill.), as described by Towbin, et al., *Proc. Nat'l Acad. Sci. U.S.A.* 76:4350-4354 (1979), except that methanol was omitted from the transfer buffer. L45 antigen was immunodetected using peroxidase-conjugated goat anti-mouse IgG as a second antibody (HyClone Lab., Logan, Utah) and 4-chloro-1-napthol as chromogen (Hawkes, *Anal. Biochem.* 123:143-146 (1982)). Immunodetection revealed that the major band at Mr=100,000 was specifically stained with L45 antibody.

B) Radioimmunoprecipitation

A549 cells were biosynthetically labeled with [$^3$H]-glucosamine and [$^3$H]-leucine, respectively, by incubation in RPMI 1640 media (glucose-free or leucine-free, RPMI 1640 Select-Amine Kit, GIBCO), supplemented with 10% dialyzed fetal bovine serum (FBS) for 5 hr at 37° C. and chased overnight in DMEM media, supplemented with 10% FBS. The cell pellets then were extracted with 50 mM sodium phosphate buffer, pH 7.2, 150 mM NaCl, 2 mM EDTA, 0.1% SDS, 1% Triton X-100, 1% sodium deoxycholate, PMSF (10 μg/ml), aprotinin (10 μg/ml). L45 antigen was immunoprecipitated by incubating the lysates with L45 antibody for 1 hr at 4° C. The antigen antibody complex was precipitated with goat anti-mouse IgG and Pansorbin (Staphylococcus aureus cells, Calbiochem, San Diego, Calif.) by sequentially incubating for 30 min, each, at 4° C. The immunoprecipitate was washed 4 times with 50 mM sodium phosphate buffer, pH 7.2, 150 mM NaCl, 2 mM EDTA, 0.1% NP40, and analyzed by SDS-PAGE under reducing and non-reducing conditions and visualized by fluorography after impregnating the gel with EN$^3$HANCE TM (New England Nuclear, Boston, Mass.).

L45 antibody specifically precipitated L45 antigen with a Mr=100,000 in both [$^3$H]-leucine and $^3$H]-glucosamine-labeled cells. These data demonstrate that the antigenic determinant recognized by L45 monoclonal antibody is located on a unique single-chain glycoprotein with Mr=100,000. The L45 antigen is associated with a variety of tumor cells including lung, breast, colon and ovary carcimona cells and melanoma and sarcoma cells.

It is apparent that many modifications and variations of this invention as set forth above may be made without departing from the spirit and scope. The specific embodiments described are given by way of example only and the invention is limited only by the terms of the appended claims.

What is claimed is:

1. A monoclonal antibody produced by hybridoma cell line ATCC No. HB 9804, which antibody binds to a determinant site on a cell surface glycoprotein antigen of human tumor cells and antibodies which bind to the same antigenic determinant as does the monoclonal antibody produced by hybridoma cell line ATCC No. HB 9804 and compete with the monoclonal antibody produced by ATCC No. HB 9804 for binding at that antigenic determinant, Fab, F(ab')$_2$, and Fv fragments and conjugates of said antibody.

2. The monoclonal antibody of claim 1 wherein said tumor cells are carcinoma cells.

3. The monoclonal antibody of claim 2 wherein said carcinoma cells are selected from the group consisting of lung, ovary, colon and breast carcinoma cells.

4. The monoclonal antibody of claim 1 wherein said tumor cells are melanoma cells.

5. The monoclonal antibody of claim 1 wherein said tumor cells are sarcoma cells.

6. The monoclonal antibody of claim 1 conjugated to a label capable of producing a detectable signal.

7. The monoclonal antibody of claim 6 wherein the label is selected from the group consisting of a radionuclide, an enzyme, a fluorescent agent and a chromophore.

8. A monoclonal antibody produced by hybridoma cell line ATCC No. HB 9804, which antibody binds to a determinant site on a cell surface glycoprotein antigen of human tumor cells, said antigen characterized by a molecular weight of about 100,000 daltons as determined by polyacrylamide gel electrophoresis, and having an amino terminal amino acid sequence as follows:

```
1            5            10
W—Y—T—V—N—S—A—Y—G—D—T—I—I—I—
         15           20           25
        —P—X—R—L—D—V—P—Q—N—L—M—F
``` in which X represents an unidentified amino acid and antibodies which bind to the same antigenic determinant as does the monoclonal antibody produced by hybridoma cell line ATCC No. HB 9804 and complete with the monoclonal antibody produced by hybridoma cell line ATCC No. HB 9804 for binding at that antigenic determinant, Fab, F(ab')$_2$, and Fv fragments and conjugates of said antibody.

9. A monoclonal antibody produced by a hybridoma cell line formed by fusion of a myeloma cell and a cell capable of producing antibody which binds to a determinant on a cell surface glycoprotein antigen of human tumor cells, said antigen having a molecular weight of about 100,000 daltons as determined by polyacrylamide gel electrophoresis, and having an amino terminal amino acid sequence as follows:

```
1            5            10
W—Y—T—V—N—S—A—Y—G—D—T—I—I—I—
         15           20           25
        —P—X—R—L—D—V—P—Q—N—L—M—F
``` in which X represents an unidentified amino acid and antibodies that are capable of binding to the same antigenic determinant as does the monoclonal antibody produced by hybridoma cell line ATCC No. HB 9804 and competing with the monoclonal antibody produced by hybridoma cell line ATCC No. HB 9804 for binding at that antigenic determinant, Fab, F(ab')$_2$, and Fv fragments and conjugates of said antibody.

10. The monoclonal antibody of claim 9 which is of class IgG.

11. The monoclonal antibody of claim 9 which is of subclass IgG2a.

12. The monoclonal antibody of claim 9 which is a murine antibody.

13. A monoclonal antibody reactive with a determinant site on a cell surface glycoprotein antigen associated with human tumor cells, said antigen characterized by a molecular weight of about 100,000 daltons as determined by polyacrylamide gel electrophoresis and having an amino terminal amino acid sequence as follows:

```
1            5            10
W—Y—T—V—N—S—A—Y—G—D—T—I—I—I—
         15           20           25
        —P—X—R—L—D—V—P—Q—N—L—M—F
``` in which X represents an unidentified amino acid and antibodies which bind to the same antigenic determinant as does the monoclonal antibody produced by hybridoma cell line ATCC No. HB 9804 and compete with the monoclonal antibody produced by hybridoma cell line ATCC No. HB 9804 for binding at that antigenic determinant, Fab, ab')$ 2, and Fv fragments and conjugates of said antibody.

14. The monoclonal antibody of claim 13 consisting of the monoclonal antibody produced by hybridoma cell line ATCC No. HB 9804.

15. The monoclonal antibody of claim 13 which is a human antibody.

16. The monoclonal antibody of claim 13 which is a mouse-human antibody.

17. A continuous cell line which produces a monoclonal antibody, wherein said monoclonal antibody binds to the same antigenic determinant as monoclonal antibody L45 produced by hybridoma cell line ATCC No. HB 9804, said cell line produced by the process of fusing. a lymphocyte derived from a mouse immunized with carcinoma cells or an immunogenic determinant thereof and a mouse myeloma cell.

18. A continuous cell line which produces a monoclonal antibody, wherein said monoclonal antibody binds to the same antigenic determinant as monoclonal antibody L45 produced by hybridoma cell line ATCC No. HB 9804, said cell line produced by the process of fusing a lymphocyte derived from a human with carcinoma and a myeloma cell.

19. A hybridoma cell line ATCC number HB 9804 which produces a monoclonal antibody which binds to a determinant on a cell surface glycoprotein antigen of human tumor cells.

20. Hybridoma cell line ATCC NO. HB 9804 formed by fusing a NSI mouse myeloma cell with a mouse splenocyte obtained from a BALB/c mouse immunized with lung adenocarcinoma CH3 cells which produces a monoclonal antibody which binds to a determinant of cell surface glycoprotein antigen of human tumor cells having a molecular weight of about 100,000 daltons having an amino terminal amino acid sequence as follows:

```
1            5            10
W—Y—T—V—N—S—A—Y—G—D—T—I—I—I—
         15           20           25
        —P—X—R—L—D—V—P—Q—N—L—M—F
``` in which X represent an unidentified amino acid as determined by polyacrylamide gel electrophoresis.

21. A continuous cell line which produces a monoclonal antibody being characterized by the capability of binding to a determinant site on a cell surface glycoprotein antigen associated with tumor cells, said antigen having a molecular weight of about 100,000 daltons having an amino terminal amino acid sequence as follows:

$$\overset{1}{W}-Y-T-V-\overset{5}{N}-S-A-Y-G-\overset{10}{D}-T-I-I-I-$$
$$\overset{15}{-P}-X-R-L-D-\overset{20}{V}-P-Q-N-L-\overset{25}{M}-F$$

in which X represents an unidentified amino acid, which comprises: a hybridoma of a lymphocyte capable of producing antibody against said antigen and a myeloma cell.

* * * * *